United States Patent [19]

Sih

[11] 4,267,395
[45] May 12, 1981

[54] 2-DECARBOXY-2-HYDROXYMETHYL-19-HYDROXY-19-METHYL-6A-CARBA-$PGI_2$ COMPOUNDS

[75] Inventor: John C. Sih, Portage, Mich.

[73] Assignee: The Upjohn Company, Kalamazoo, Mich.

[21] Appl. No.: 126,465

[22] Filed: Mar. 3, 1980

Related U.S. Application Data

[62] Division of Ser. No. 54,720, Jul. 5, 1979, Pat. No. 4,225,507.

[51] Int. Cl.³ .............................................. C07C 33/05
[52] U.S. Cl. .................................. 568/819; 568/374; 562/501
[58] Field of Search ................. 568/819, 374; 562/501

[56] References Cited

U.S. PATENT DOCUMENTS 3,993,687  11/1976  Schneider ............................ 562/501
4,149,017  4/1979  Woessner et al. .................... 568/819

*Primary Examiner*—Natalie Trousof
*Assistant Examiner*—James H. Reamer
*Attorney, Agent, or Firm*—Robert A. Armitage

[57] ABSTRACT

The present invention provides novel 2-decarboxy-2-hydroxymethyl-19-hydroxy-19-methyl-6a-carba-$PGI_1$ compounds which are useful for pharmacological purposes, e.g., anti-asthmatic indications.

4 Claims, No Drawings

2-DECARBOXY-2-HYDROXYMETHYL-19-HYDROXY-19-METHYL-6A-CARBA-PGI$_2$ COMPOUNDS

DESCRIPTION

CROSS REFERENCE TO RELATED APPLICATION

The present invention is a divisional application of U.S. Ser. No. 054,720, filed July 5, 1979, now U.S. Pat. No. 4,225,507.

BACKGROUND OF THE INVENTION

The present invention provides novel prostacyclin analogs. Particularly, the present invention relates to prostacyclin analogs substituted at the C-19 position by hydroxy.

Particularly, the present invention relates to 2-decarboxy-2-hydroxymethyl-19-hydroxy-19-methyl-6a-carba-PGI$_2$ compounds. The novel prostacyclin analogs are useful for pharmacological purposes, e.g., as antiasthmatic agents. The preparation and use of these compounds is incorporated here by reference from U.S. Pat. No. 4,225,507.

PRIOR ART

For background on prostacyclin, see for example R. A. Johnson, et al., Prostaglandins 12, 915–928 (1976) and R. A. Johnson, et al., J. Am. Chem. Soc. 100, 7690–7704 (1978), and, as to pharmacological activity, the references cited therein. For analogs of prostacyclin, see, for example, J. Fried, et al., Proc. Natl. Acad. Sci. U.S.A. 74, 2199–2203, K. C. Nicolaou, et al., J.C.S. Chem. Comm. 1977, 331–332, N. A. Nelson, J. Am. Chem. Soc. 99, 7362–7363 (1977), and K. Kojima, et al., Tetra. Letters, 1978, (1977), and K. Kojima, et al., Tetra. Letters, 1978, 3743–3746. Regarding the nomenclature for analogs of PGI$_2$, see R. A. Johnson, et al., Prostaglandins 15, 737–740 (1978).

SUMMARY OF THE INVENTION

The present invention particularly provides a prostacyclin-type compound of the formula

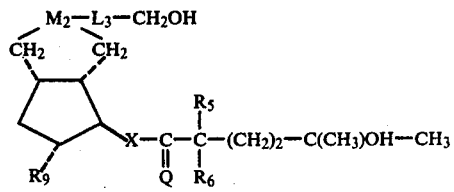

wherein L$_3$ is
(1) —(CH$_2$)$_n$—, wherein n is one to 5, inclusive,
(2) —(CH$_2$)$_p$—CF$_2$—, wherein p is 2, 3, or 4, or
(3) —CH$_2$—CH=CH—;
wherein M$_2$ is

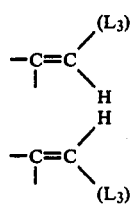

wherein Q is oxo, $\alpha$—H:$\beta$—H, $\alpha$—OH:$\beta$—R$_4$, or $\alpha$—R$_4$:$\beta$—OH,
wherein R$_4$ is hydrogen or alkyl of one to 4 carbon atoms, inclusive,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein R$_2$ is hydrogen or hydroxyl; and wherein X is
(1) trans—CH=CH—,
(2) cis—CH=CH—,
(3) —C≡C—, or
(4) —CH$_2$CH$_2$—.

DESCRIPTION OF THE PREFERRED EMBODIMENTS

The present invention particularly relates to the following compounds:
(5E)-2-Decarboxy-2-hydroxymethyl-6a-carba-19-hydroxy-19-methyl-PGI$_2$, and
(5E)-2-Decarboxy-2-hydroxymethyl-6a-carba-16,16-difluoro-19-hydroxy-19-methyl-PGI$_2$.

We claim:
1. A prostacyclin-type compound of the formula

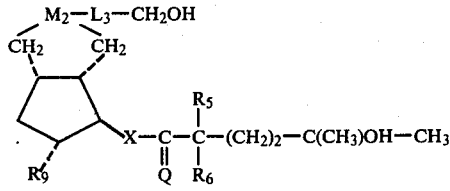

wherein L$_3$ is
(1) —(CH$_2$)$_n$—, wherein n is one to 5, inclusive,
(2) —(CH$_2$)$_p$—CF$_2$—, wherein p is 2, 3, or 4, or (3) —CH$_2$—CH=CH—;
wherein M$_2$ is

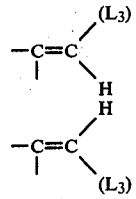

wherein Q is oxo, $\alpha$—H:$\beta$—H, $\alpha$—OH:$\beta$—R$_4$, or $\alpha$—R$_4$:$\beta$—OH,
wherein R$_4$ is hydrogen or alkyl of one to 4 carbon atoms, inclusive,
wherein R$_5$ and R$_6$ are hydrogen, alkyl of one to 4 carbon atoms, inclusive, or fluoro, being the same or different, with the proviso that one of R$_5$ and R$_6$ is fluoro only when the other is hydrogen or fluoro;
wherein R$_2$ is hydrogen or hydroxyl; and wherein X is
(1) trans—CH=CH—,
(2) cis—CH=CH—,
(3) —C≡C—, or
(4) —CH$_2$CH$_2$—.

2. A compound according to claim 1, wherein Q is $\alpha$—OH:$\beta$—H, R$_9$ is hydroxyl, and X is trans—CH=CH—.

3. (5E)-2-Decarboxy-2-hydroxymethyl-6a-carba-19-hydroxy-19-methyl-PGI$_2$, a compound according to claim 2.

4. (5E)-2-Decarboxy-2-hydroxymethyl-6a-carba-16,16-difluoro-19-hydroxy-19-methyl-PGI$_2$, a compound according to claim 2.

* * * * *

UNITED STATES PATENT OFFICE
CERTIFICATE OF CORRECTION

Patent No. 4,267,395     Dated 12 May 1981

Inventor(s) John C. Sih

It is certified that error appears in the above-identified patent and that said Letters Patent are hereby corrected as shown below:

Column 1, lines 45-53, and Column 2, lines 24-32, the formula should read as follows:

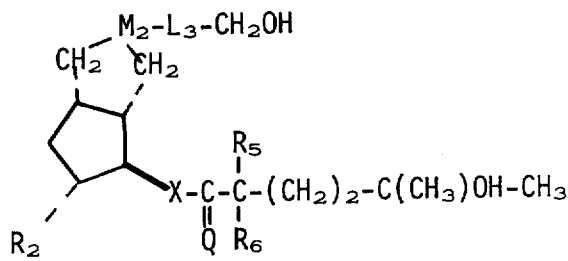

Signed and Sealed this

Twenty-eighth Day of July 1981

[SEAL]

Attest:

Attesting Officer

GERALD J. MOSSINGHOFF

Commissioner of Patents and Trademarks